US00PP18470P2

(12) United States Plant Patent
Marten

(10) Patent No.: US PP18,470 P2
(45) Date of Patent: Feb. 5, 2008

(54) ***COLEUS* PLANT NAMED 'MD CURCOR06'**

(50) Latin Name: *Solenostemon scutellarioides*
Varietal Denomination: MD CURCOR06

(76) Inventor: Walter Marten, Staerkstr. 19/22, D-16548 Glienicke (DE)

( * ) Notice: Subject to any disclaimer, the term of this patent is extended or adjusted under 35 U.S.C. 154(b) by 124 days.

(21) Appl. No.: 11/395,075

(22) Filed: Mar. 31, 2006

(51) Int. Cl.
*A01H 5/00* (2006.01)

(52) U.S. Cl. ..... Plt./373
(58) Field of Classification Search ..... Plt./373
See application file for complete search history.

*Primary Examiner*—Anne Marie Grunberg
*Assistant Examiner*—Georgia Helmer

(57) ABSTRACT

A new and distinct *Coleus* plant cultivar is disclosed, characterized by deeply lobed, undulating leaves, a wide mix of colors per leaf, a compact growth habit and short internodes.

1 Drawing Sheet

Latin name of the genus and species: *Solenostemon scutellarioides.*
Variety denomination: 'MD CURCOR06'.

BACKGROUND OF THE INVENTION

The new cultivar 'MD CURCOR06' was discovered as a naturally occurring whole plant mutation of the *Coleus* plant variety 'Bienvenue' (not patented). The new cultivar was discovered in May of 2002 as a single plant in a cultivated area of Glienicke, Germany.

Asexual reproduction of the new cultivar 'MD CURCOR06' by terminal cuttings was first performed in 2002 in Oxnard, Calif., and has shown that the unique features of this new cultivar are stable and reproduced true to type on successive generations.

SUMMARY OF THE INVENTION

The cultivar 'MD CURCOR06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MD CURCOR06'. These characteristics in combination distinguish 'MD CURCOR06' as a new and distinct *Coleus* cultivar:

1. Deeply lobed, undulating leaves;
2. Wide mix of colors per leaf;
3. Compact growth habit; and
4. Short internodes.

Plants of the new cultivar 'MD CURCOR06' are similar to plants of the parent variety, 'Bienvenue,' in most horticultural characteristics, however plants of the new cultivar 'MD CURCOR06' are much shorter than the parent variety. Also, the leaves of the parent are longer than the new variety. Finally, the foliage of the parent variety was red brown, with yellow-green margins and irregular brown patches on the middle rib while the foliage of 'MD CURCOR06' is a pale yellow with coral patches in the middle and a darker green margin.

In comparison to the commercially available variety 'Mrs. Harding' (not patented), 'MD CURCOR06' has much more deeply lobed and undulating foliage. Additionally, the new variety 'MD CURCOR06' has a darker green color on the margin of the foliage and a light coral color at the center of the foliage compared to the darker bronze of 'Mrs. Harding.'

BRIEF DESCRIPTION OF THE PHOTOGRAPH

The accompanying photograph illustrates in full color a typical plant of 'MD CURCOR06' grown in a four-inch pot. One cutting was used in the pot, planted mid December and grown in a greenhouse. During the production of the plants, day temperatures were about 25° C., night temperatures were about 12° C. and light levels ranged from 4,000 to 6,000 footcandles. The colors are as nearly true as is reasonably possible in a color representation of this type. The age of the plant in the photograph is 12 weeks old.

DETAILED BOTANICAL DESCRIPTION

In the following description, color references are made to The Royal Horticultural Society Colour Chart except where general terms of ordinary dictionary significance are used. The following observations and measurements describe 'MD CURCOR06' plants grown in Oxnard, Ventura County, Calif., during the months of December through February. The growing temperature ranged from 12° C. to 15° C. at night to 12° C. to 20° C. during the day. Measurements and numerical values represent averages of typical *coleus* plants.

Botanical classification: *Coleus* cultivar 'MD CURCOR06.'
Commercial classification: *Coleus.*

PROPAGATION

Type cutting: Terminal cuttings.
Time to initiate roots: 4 days with 18° C.
Time to develop roots: 6 to 8 days with 16° C. to 18° C.
Root description: Fine, fibrous, white in color.
Rooting habit: Freely branching.

PLANT

Form: Annual potted or garden plant.
Growth habit: Low and outwardly spreading plant habit.
Growth rate: Moderate.
Plant height: About 12 cm.
Plant diameter: About 15 cm.

Branching habit: Freely branching with about six lateral branches per plant.
Length of lateral branches: About 6 cm.
Diameter: About 0.5 cm.
Internode length: About 1.3 cm.
Strength: Strong.
Aspect: Initially upright then outwardly spreading.
Shape, in cross-section: Squarish.
Texture: Lightly pubescent.
Color: Near Yellow-Green 145B.

FOLIAGE

Arrangement: Opposite; simple.
Length: About 4.7 cm.
Width: About 4 cm.
Shape: Ovate.
Apex: Broadly acute.
Base: Truncate.
Margin: Crenate.
Texture:
*Upper surface.*—Lightly pubescent.
*Lower surface.*—Lightly pubescent.
Venation pattern: Pinnate; netted.
Color:
*Developing foliage on the upper surface.*—Towards the margins: Near Green 143A. Towards the center: Near Yellow-Orange 22A. Center: Near Red 46A. Towards the base: Near Red 46A. Venation: Near Greyed-Red 181A.
*Developing foliage on the lower surface.*—Towards the margins: Near Green 143A. Towards the center: Near Green 145C. Center: Near Green 145C. Towards the base: Near Green 145C. Venation: Near Green 145C.
*Fully expanded foliage on the upper surface.*—Towards the margins: Near Green 143A. Towards the center: Near Yellow-Orange 20A. Center: Near Red 46A. Towards the base: Near Yellow-Orange 20A. Venation: Near Greyed-Red 180A.
*Fully expanded foliage on the lower surface.*—Towards the margins: Near Green 143B. Towards the center: Near Green-Yellow 1D. Center: Near Green-Yellow 1D. Towards the base: Near Green-Yellow 1C. Venation: Near Green-Yellow 1C.
Petiole length: About 2 cm.
Petiole diameter: About 0.3 cm.
Petiole color:
*Towards the apex.*—Near Greyed-Red 178A.
*Towards the base.*—Near Yellow-Green 145C.
Flower description: Flower development has not been observed.

OTHER CHARACTERISTICS

Disease resistance: Neither resistance nor susceptibility to diseases or pests has been observed in this variety.
Drought tolerance/cold tolerance: Plants of the new *Coleus* have been observed to have no drought tolerance and do not produce at a temperature lower than 8° C.
Fruit/seed production: Commercially, this plant is not used or observed in a stage where seeds would be produced. Therefore, seed production has not been observed.

What is claimed is:

1. A new and distinct cultivar of *Coleus* plant named 'MD CURCOR06' as herein illustrated and described.

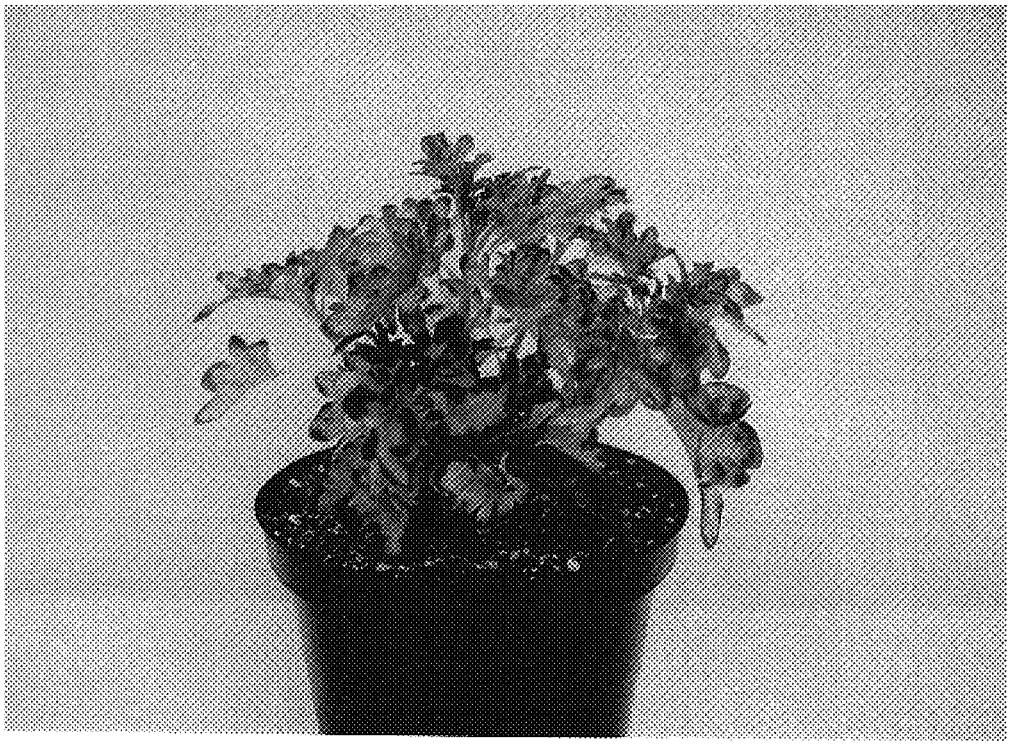

* * * * *